United States Patent [19]

Curtis

[11] Patent Number: 4,915,255
[45] Date of Patent: Apr. 10, 1990

[54] TRANSPORTABLE SPECIMEN CONTAINER INCLUDING REMOVABLE CENTRIFUGE TUBE

[75] Inventor: Robert E. Curtis, San Jose, Calif.

[73] Assignee: CytoSciences, Inc., San Jose, Calif.

[21] Appl. No.: 247,818

[22] Filed: Sep. 22, 1988

[51] Int. Cl.⁴ .......................... B65D 3/04; B65D 3/24
[52] U.S. Cl. .................................... 220/408; 220/410;
220/23.83; 220/23.86; 220/8; 206/521
[58] Field of Search ................... 220/83, 23.83, 23.86,
220/408, 8, 410; 215/12.1; 206/521

[56] References Cited

U.S. PATENT DOCUMENTS

| | | | |
|---|---|---|---|
| 2,217,755 | 10/1940 | Larsen | 220/410 |
| 3,518,164 | 6/1970 | Andelin et al. | 220/408 |
| 3,621,994 | 11/1971 | Brown | 220/410 |
| 3,730,374 | 5/1973 | Picciano et al. | 220/408 |
| 3,819,081 | 6/1974 | Runte | 220/408 |

Primary Examiner—Stephen Marcus
Assistant Examiner—Stephen Castellano
Attorney, Agent, or Firm—Flehr, Hohbach, Test, Albritton & Herbert

[57] ABSTRACT

A specimen container is disclosed wherein a sample tube is releasably held by the neck of a support which is disposed in an outer housing. A cap is threadably received by the support and cooperates with the housing to house the sample tube.

4 Claims, 3 Drawing Sheets

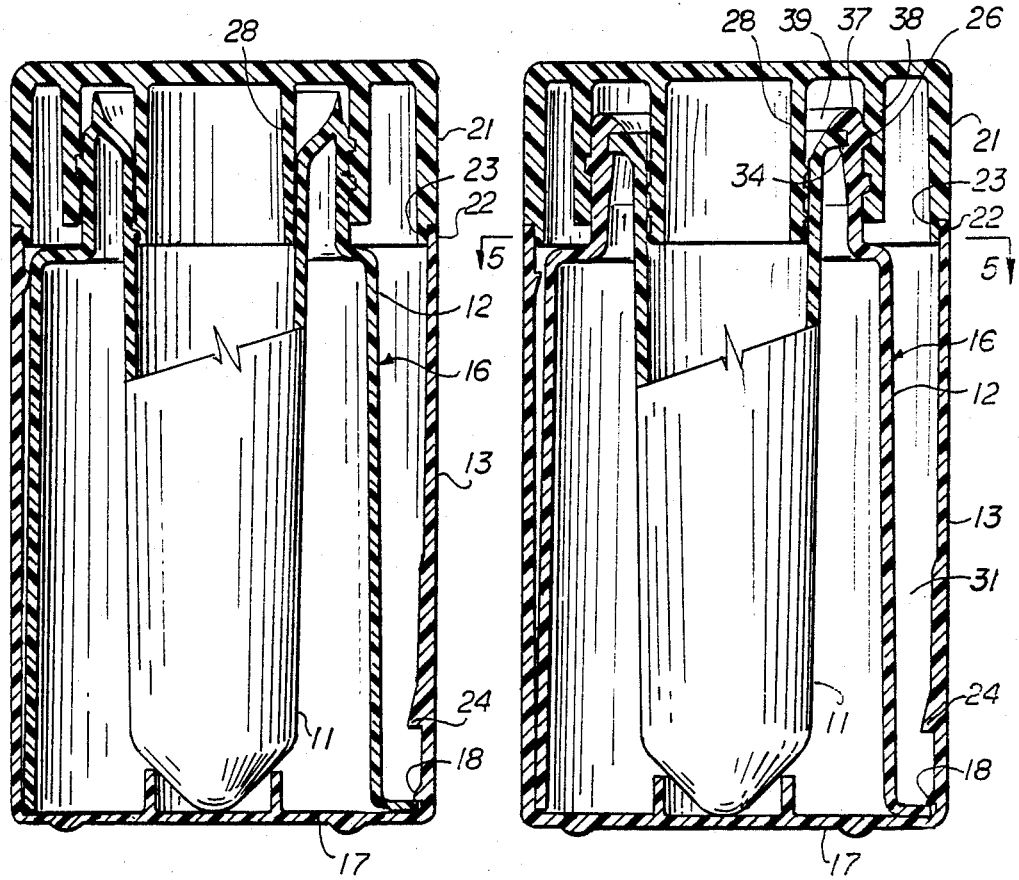
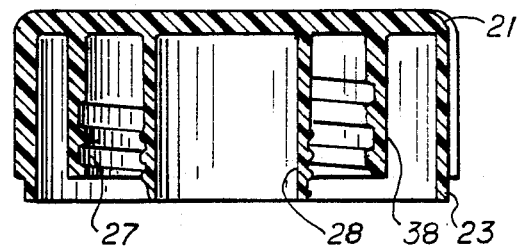

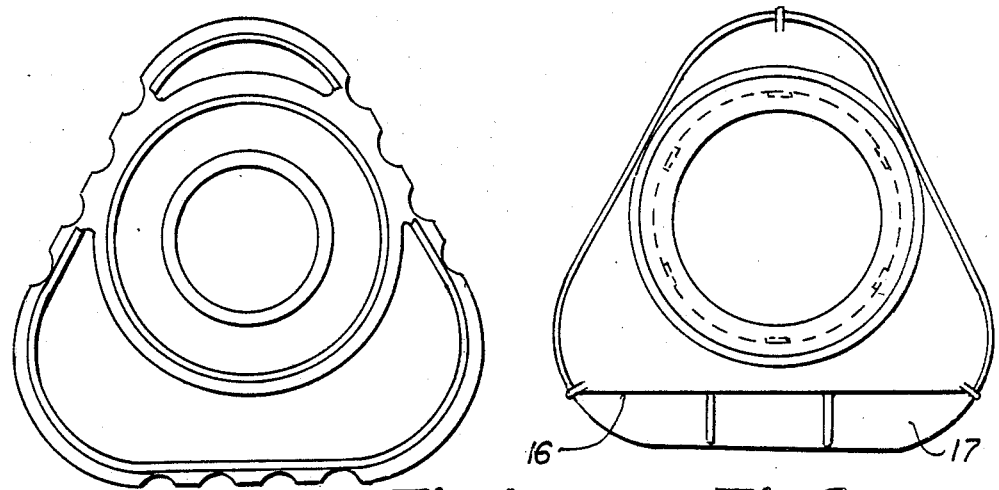
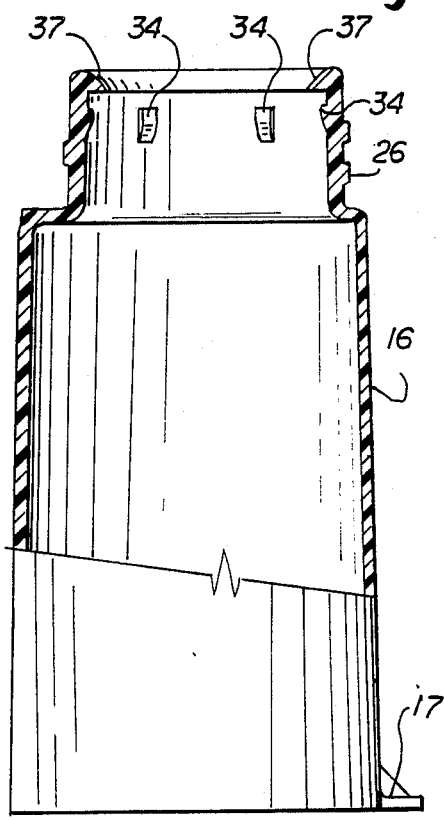
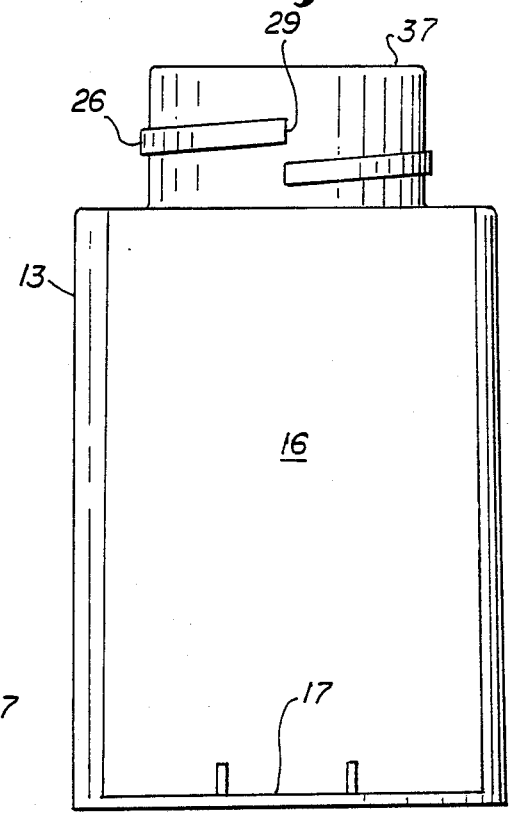

TRANSPORTABLE SPECIMEN CONTAINER INCLUDING REMOVABLE CENTRIFUGE TUBE

This invention relates generally to a transportable specimen collector and container and more particularly to a transportable specimen container which includes a snap on centrifuge tube which can be easily removed from the container body for a specimen analysis.

Since the beginning of the medical profession there has existed a necessity to transport specimens from the patient to a laboratory for analysis. Current containers have been in the form of glass or plastic containers with snap on or screw on caps. Characteristically their transport has taken the form of hand delivery and/or mail in cardboard mailing tubes or containers. Both methods have unique requirements with the latter the most demanding.

Specimen collector devices in todays marketplace are clumsy at best in their attempt to be leak proof, safe, transportable and easy to use. There exists a need in the marketplace for a properly constructed specimen container.

From a general standpoint the collection device should be break resistant, labelable and leakproof. There should be a method for identifying the specimen and a corresponding request from the originating party as to what analysis is required. Further, the device should be biologically safe, that is, retain the specimen without undue hazard to the public during transport. It should be easy to use, aesthetically pleasing, lightweight and inexpensive.

The assignee of the present invention is presently marketing a triangular prismatic transportable container with each leg of the triangle being approximately three inches and the height approximately four and three-quarter inches. The container includes a centrifuge tube formed integrally with a support member which fits into an outer housing. A cap is provided for sealing the centrifuge tube and completing the container housing.

OBJECTS AND SUMMARY OF THE INVENTION

It is a general object of the present invention to provide an improved transportable specimen container having a removable centrifuge tube.

It is a further object of the present invention to provide an improved transportable specimen container which carries a snap on centrifuge tube for removal and sample analysis.

The foregoing and other objects of the invention are achieved by a transportable specimen container comprising an elongated centrifuge tube having an open upper end, a centrifuge tube support comprising an enclosure for releasably engaging and supporting the upper end of the centrifuge tube said support surrounding and spaced from said tube to protect the same and extending the full length of the centrifuge tube. An outer housing having an open end for receiving the enclosure and a bottom, said enclosure and housing spaced so as to define therebetween an open space for receiving a medical requisition and a cap threadably received by said enclosure and adapted to seal the upper end of said tube and to cooperate with said housing to completely house the centrifuge tube for transport.

The foregoing and other objects of the invention will be more clearly understood from the following description taken in conjunction with the drawings.

DESCRIPTION OF THE DRAWINGS

FIG. 1 is an elevational view in section showing a transportable specimen container in accordance with the prior art.

FIG. 2 is a section view similar to FIG. 1 showing a transportable specimen container in accordance with the present invention.

FIG. 3 is a sectional view of the cap shown in FIGS. 1 and 2.

FIG. 4 is a bottom view of the cap.

FIG. 5 is a sectional view taken generally along the line 5—5 of FIG. 2.

FIG. 6 is an elevational view of the centrifuge tube support.

FIG. 7 is a sectional view of the centrifuge tube support.

DESCRIPTION OF PREFERRED EMBODIMENT

Figure 8:
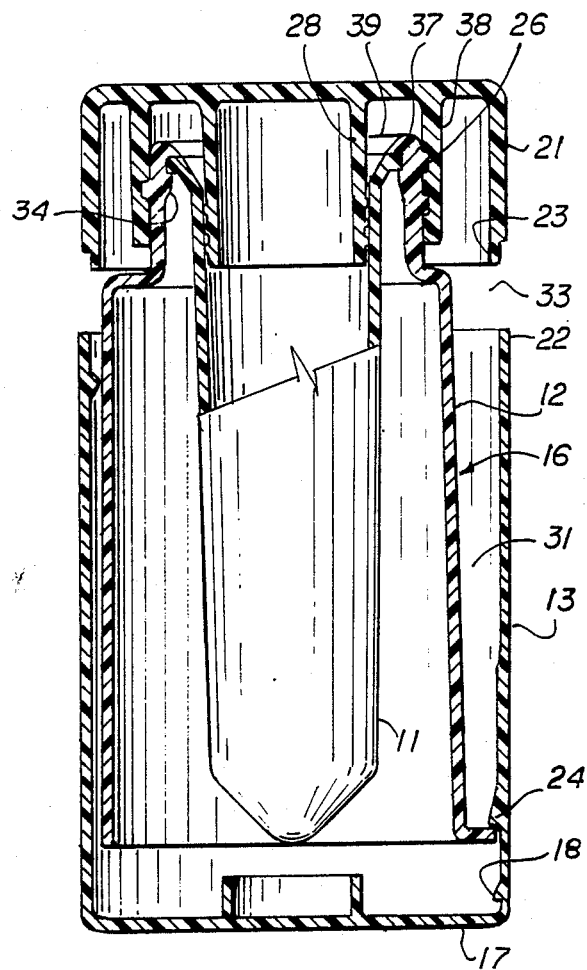
FIG. 8 is a side elevational view showing the centrifuge tube and support lifted from the housing to permit rotation of the cap for sealing and unsealing.

The present invention comprises an improvement over the prior art as exemplified by the specimen container presently being sold by assignee. The transportable specimen container as presently sold includes a specimen tube in the form of a centrifuge tube 11, FIG. 1, integral with a surrounding support 12 which extends the full length of the tube. The centrifuge tube and support are housed within an outer housing 13 which is triangular in shape as shown in FIG. 4. Referring particularly to FIGS. 2 and 5 it is noted that the shape of the support 12 is triangular with the exception that one face 16 defines a lower lip 17. When the support is fully seated within the outer housing 13 the lip 17 is engaged by a projection 18 formed in the outer envelope to lock the support in the lowered position. When the cap has been applied as shown in FIGS. 1 and 2 and the support lowered as shown, the cap 21 engages the outer housing and is locked against rotation. In view of the fact that the cap and housing are triangular in shape, the locking is achieved by the interaction of the top edge 22 of the housing and the lip 23 formed in the cap. To remove the cap the cap is grasped and the support and cap are urged upwardly to overcome the retaining force of the tab or projection 18. The support is then lifted until the lip 17 engages the stop 24, FIG. 8. At this point the cap can be rotated and removed whereby to expose the upper funnel shaped end of the centrifuge tube 11 for a patient to deposit his specimen in the centrifuge tube.

Referring more particularly to FIGS. 6 and 7 the upper end of the support is provided with an external thread 26 which is engaged by the cooperating internal threaded section 27 or the cap 21. The cap includes an inner sealing sleeve 28 which slides inside of the centrifuge tube 11 and forms a seal therewith. As shown, the neck of the centrifuge tube is engaged by the sealing member which creates a triple sealing area.

Since the top of the support 12 is off center, alignment of the cap ensures visually that the cap is completely closed by the observing that all three sides of the top align with the outer housing. The threads in the cap and on the neck are so constructed that they form a stop when the end of the thread on the cap engages the end 29 of the thread on the support neck. This prevents over tightening of the cap.

In use, the support is lifted until the lip 17 engages the stop 24; the cap is unscrewed; cap 21 is removed; specimen is inserted; the cap is then screwed on until is reaches its stop and is aligned with the sides of the housing 13; the assembly is lowered; and, the specimen collector is locked in closed position by the interaction of the lip 17 and tab 18.

It is to be noted that because of the shape of the outer housing 13 and the wall 16, there is a space 31, FIG. 8, between the support 12 and the housing 13 along one side of the triangular housing. When the assembly is open a doctor or nurse can insert instructions into the space 31 preferably prior to applying the cap or subsequent thereto through the slot 33, FIG. 8. Thus, when the specimen is received by the laboratory the technician has the instructions for the test to be performed.

In the prior art the centrifuge tube was removed from the integral support by cutting or sawing at the top. In accordance with the present invention, the support and tube are formed in two pieces and snapped to one another.

Referring more particularly to FIGS. 2 and 7, the support is formed with a neck having inwardly facing projections 36 and inwardly facing upper lip 37. The tube is formed with an outwardly extending rim 38. The tube is assembled to the support by inserting it from the bottom and forcing it to snap over the projections 36 so that it is held with the lip 37 in intimate contact with the rim 38 to form a seal along the interface 39.

When the collector is received in the lab, the lab technician removes the complete assembly of support and centrifuge tube from the outer housing by pulling upwardly with a force sufficient to cause the lip 17 to ride past the projections 18 and 24. The cap is then removed and the test tube tilted so that it snaps past the retaining projections and is removed from the bottom of the support for analysis.

Thus, there has been provided an improved transportable specimen container.

I claim:

1. A specimen container comprising an elongated centrifuge tube having one open end;
   a centrifuge tube support including a neck with internal projections for releasably engaging the upper end of the centrifuge tube and supporting same within said support whereby it is surrounded by and spaced therefrom;
   an outer housing having an open end for receiving the support and a bottom; and
   a cap threadably received by said support and adapted to seal the upper end of said tube and to cooperate with said housing to completely house the centrifuge tube for transport.

2. A specimen container as in claim 1 in which said support neck includes a lip and said centrifuge tube includes a rim for seating said projections and said lip.

3. A specimen container comprising an elongated sample tube having one open end;
   a sample tube support including a neck with internal projections for releasably engaging the upper end of the sample tube and supporting same within said support whereby it is surrounded by and spaced therefrom;
   an outer housing having an open end for receiving the support and a bottom; and
   a cap threadably received by said support and adapted to seal the upper end of said tube and to cooperate with said housing to completely house the sample tube for transport.

4. A specimen container as in claim 3 in which said support neck includes a lip and said sample tube includes a rim for seating between said projections and said lip.

* * * * *